(12) United States Patent
Szudajski et al.

(10) Patent No.: US 9,970,888 B2
(45) Date of Patent: May 15, 2018

(54) SYSTEM AND METHOD FOR WELLSITE CORE SAMPLE ANALYSIS

(71) Applicant: GE Energy Oilfield Technology, Inc., Houston, TX (US)

(72) Inventors: Thomas Szudajski, Houston, TX (US); John Boot, Atlanta, GA (US)

(73) Assignee: GE ENERGY OILFIELD TECHNOLOGY, INC., Houston, TX (US)

( * ) Notice: Subject to any disclaimer, the term of this patent is extended or adjusted under 35 U.S.C. 154(b) by 241 days.

(21) Appl. No.: 14/536,340

(22) Filed: Nov. 7, 2014

(65) Prior Publication Data

US 2016/0131793 A1    May 12, 2016

(51) Int. Cl.
| | | |
|---|---|---|
| *G01N 23/04* | (2006.01) | |
| *G01V 5/04* | (2006.01) | |
| *G01V 5/08* | (2006.01) | |
| *G01V 5/12* | (2006.01) | |
| *G01V 5/14* | (2006.01) | |
| *G01N 21/65* | (2006.01) | |
| *G01N 21/71* | (2006.01) | |

(Continued)

(52) U.S. Cl.
CPC ....... *G01N 23/046* (2013.01); *G01N 21/3563* (2013.01); *G01N 21/65* (2013.01); *G01N 21/718* (2013.01); *G01V 5/005* (2013.01); *G01V 5/0016* (2013.01); *G01V 5/0025* (2013.01); *G01V 5/0033* (2013.01); *G01V 5/04* (2013.01); *G01V 5/12* (2013.01); *G01V 5/14* (2013.01)

(58) Field of Classification Search
CPC ........ G01N 23/046; G01V 5/005; G01V 5/04; G01V 5/0016; G01V 5/0025; G01V 5/0033
USPC .......................................... 378/4, 62, 53, 55
See application file for complete search history.

(56) References Cited

U.S. PATENT DOCUMENTS 3,704,898 A    12/1972 Schmidt
3,746,369 A    7/1973 Neff
(Continued)

FOREIGN PATENT DOCUMENTS

GB    2135049    8/1984

OTHER PUBLICATIONS

Reddy, B., "An FFT-Based Technique for Translation, Rotation, and Scale-Invariant Image Registration," IEEE Transactions on Image Processing, vol. 5, No. 8, Aug. 1996, pp. 1266-1271.

(Continued)

*Primary Examiner* — Allen C. Ho
(74) *Attorney, Agent, or Firm* — Hogan Lovells US LLP

(57) ABSTRACT

A method and system for analyzing a core sample from a wellbore, where the analysis takes place in the field and proximate the wellbore. The system includes trailers adjacent one another and on a drilling pad, so that real time analysis of the core sample can occur after being extracted from the wellbore. One of the trailers can include a scanning unit for scanning the core sample and obtaining information within the core sample. Other trailers can include units that further analyze the core sample, such as by grinding, laser induced breakdown spectroscopy, Raman spectroscopy, and scanning the core material nano-structure. The core sample scanning involves a computed tomography (CT) scan, where a length of core sample is analyzed in the scanning unit.

18 Claims, 6 Drawing Sheets

(51) Int. Cl.
*G01N 21/3563* (2014.01)
*G01V 5/00* (2006.01)

(56) References Cited

U.S. PATENT DOCUMENTS

| | | | |
|---|---|---|---|
| 4,244,417 A | 1/1981 | Taylor | |
| 4,571,491 A | 2/1986 | Vinegar et al. | |
| 4,583,242 A | 4/1986 | Vinegar et al. | |
| 4,616,134 A | 10/1986 | Pruett et al. | |
| 4,909,557 A | 3/1990 | De Weck et al. | |
| 4,924,187 A | 5/1990 | Sprunt et al. | |
| 4,977,586 A | 12/1990 | Curry | |
| 5,025,150 A | 6/1991 | Oldham et al. | |
| 5,109,398 A | 4/1992 | Hunt et al. | |
| 5,153,899 A | 10/1992 | Curry | |
| 5,318,123 A | 6/1994 | Venditto et al. | |
| 5,360,066 A | 11/1994 | Venditto et al. | |
| 5,386,875 A | 2/1995 | Venditto et al. | |
| 5,409,251 A | 4/1995 | Thorndyke | |
| 5,509,687 A | 4/1996 | Thorndyke | |
| 5,712,893 A | 1/1998 | Dykster et al. | |
| 5,947,213 A | 9/1999 | Angle et al. | |
| 6,118,839 A | 9/2000 | Dafni et al. | |
| 6,430,255 B2* | 8/2002 | Fenkart | G01N 23/046 378/203 |
| 6,430,547 B1 | 8/2002 | Busche | |
| 6,481,887 B1* | 11/2002 | Mirabella | A61B 6/4405 296/24.38 |
| 6,816,787 B2 | 11/2004 | Ramamoorthy | |
| 6,940,941 B2* | 9/2005 | Gregerson | A61B 6/032 250/363.05 |
| 7,082,185 B2 | 7/2006 | Freifeld et al. | |
| 7,113,569 B2* | 9/2006 | Okumura | A61B 6/032 378/150 |
| 7,172,038 B2 | 2/2007 | Terry et al. | |
| 7,175,347 B2* | 2/2007 | Tybinkowski | A61B 6/032 378/196 |
| 7,564,944 B2 | 7/2009 | Kato | |
| 7,714,304 B2 | 5/2010 | Poglitsch | |
| 7,733,490 B2* | 6/2010 | Goodwin | E21B 49/10 166/250.01 |
| 7,853,045 B2 | 12/2010 | Touati | |
| 7,866,386 B2 | 1/2011 | Beer et al. | |
| 7,959,864 B2* | 6/2011 | Jiang | C09K 8/52 422/68.1 |
| 8,068,579 B1 | 11/2011 | Yun et al. | |
| 8,081,796 B2* | 12/2011 | Derzhi | E21B 49/005 378/53 |
| 8,081,802 B2* | 12/2011 | Dvorkin | G01N 23/046 175/249 |
| 8,085,974 B2* | 12/2011 | Dvorkin | G06T 7/0004 378/21 |
| 8,155,377 B2* | 4/2012 | Dvorkin | E21B 47/00 175/249 |
| 8,162,080 B2* | 4/2012 | Castillo | E21B 25/10 175/249 |
| 8,170,799 B2* | 5/2012 | Dvorkin | G01V 1/30 702/11 |
| 8,234,912 B2* | 8/2012 | Suarez-Rivera | G01N 3/46 73/78 |
| 8,326,538 B2* | 12/2012 | Hobbs | E21B 47/12 175/40 |
| 8,327,932 B2 | 12/2012 | Karanikas et al. | |
| 8,331,626 B2* | 12/2012 | Wojcik | G01N 23/046 382/109 |
| 8,540,425 B2* | 9/2013 | Groot | A61B 6/107 378/203 |
| 8,542,793 B1 | 9/2013 | Jin | |
| 8,562,078 B2 | 10/2013 | Burns et al. | |
| 8,590,382 B2* | 11/2013 | Zaleski, Jr. | E21B 43/119 166/250.01 |
| 8,636,323 B2 | 1/2014 | Prince-Wright et al. | |
| 8,657,000 B2 | 2/2014 | Willingham et al. | |
| 8,725,477 B2* | 5/2014 | Zhang | E21B 49/00 703/10 |
| 8,911,206 B2* | 12/2014 | Campbell | F03D 11/00 415/204 |
| 8,938,045 B2* | 1/2015 | Dvorkin | G01N 23/046 250/253 |
| 9,063,247 B2* | 6/2015 | Li | G01V 1/30 |
| 9,103,176 B2* | 8/2015 | Delmar | E21B 25/00 |
| 9,127,529 B2* | 9/2015 | Guzman | E21B 49/02 |
| 9,170,215 B2* | 10/2015 | O'Hare | G01N 23/046 |
| 9,196,058 B2* | 11/2015 | Mezghani | G06T 7/602 |
| 9,291,585 B2* | 3/2016 | Singh | G01N 25/00 |
| 9,341,549 B2* | 5/2016 | Lakshtanov | G01N 1/286 |
| 9,507,047 B1* | 11/2016 | Dvorkin | |
| 9,573,434 B2* | 2/2017 | Boot | B60S 9/12 |
| 9,746,431 B2* | 8/2017 | Grader | G01N 23/046 |
| 2002/0018542 A1 | 2/2002 | Fenkart et al. | |
| 2003/0107735 A1 | 6/2003 | Bland et al. | |
| 2004/0218716 A1 | 11/2004 | Freifeld et al. | |
| 2005/0127620 A1 | 6/2005 | Amundson | |
| 2008/0217559 A1 | 9/2008 | Poglitsch et al. | |
| 2009/0078467 A1 | 3/2009 | Castillo | |
| 2010/0250139 A1 | 9/2010 | Hobbs et al. | |
| 2011/0150177 A1 | 6/2011 | Groot | |
| 2012/0136196 A1 | 5/2012 | Foxall et al. | |
| 2012/0148398 A1 | 6/2012 | Campbell et al. | |
| 2012/0230151 A1 | 9/2012 | Almaguer | |
| 2013/0083888 A1 | 4/2013 | Jin | |
| 2013/0182819 A1 | 7/2013 | Dvorkin et al. | |
| 2013/0301794 A1* | 11/2013 | Grader | G01N 23/087 378/5 |
| 2014/0119501 A1 | 5/2014 | O'Hare et al. | |
| 2014/0367086 A1 | 12/2014 | Arian et al. | |
| 2015/0044004 A1 | 2/2015 | Pham et al. | |
| 2015/0177409 A1 | 6/2015 | Sofiienko | |
| 2015/0185122 A1 | 7/2015 | Lakshtanov et al. | |
| 2016/0131793 A1 | 5/2016 | Szudajski | |

OTHER PUBLICATIONS

Wang, Qiang et al., "Automatic Registration of Remote Sensing Image with Moderate Resolution," College of Geoscience and Surveying Engineering, CUMT, Beijing, China; Apr. 24-26, 2012; pp. 404-409.

Renard et al., "3D imaging of fracture propagation using synchroton X-ray microtomography," Earth and Planetary Science Letters, 286, 2009, pp. 285-291.

* cited by examiner

SYSTEM AND METHOD FOR WELLSITE CORE SAMPLE ANALYSIS

BACKGROUND OF THE INVENTION

1. Field of Invention

The present disclosure relates in general to a method and system for analyzing a core sample from a wellbore. More specifically, the present disclosure relates to a method and system for analyzing a core sample proximate to a wellbore from where the core sample was obtained.

2. Description of Prior Art

Various techniques are currently in use for identifying the presence of hydrocarbons in subterranean formations. Some techniques employ devices that emit a signal from a seismic source, and receive reflections of the signal on surface. Others involve disposing logging devices downhole in a wellbore intersecting the subterranean formation, and interrogating the formation from within the wellbore. Example downhole exploration devices include seismic tools that can transmit and receive seismic signals, or ones that simply receive a seismic signal generated at surface. Other devices collect and sample fluid from within the formation, or from within the wellbore. Nuclear tools are also employed that direct radiation into the formation, and receive radiation that scatters from the formation. Analyzing the scattered radiation can provide information about fluids residing in the formation adjacent the wellbore, the type of fluid, and information about other materials next to the wellbore, such as gravel pack.

Logging downhole also is sometimes done while the wellbore itself is being drilled. The logging devices are usually either integral with a drill bit used during drilling, or on a drill string that rotates the drill bit. The logging devices typically are either nuclear, seismic, can in some instances optical devices. In some instances, a core is taken from the wellbore and analyzed after being retrieved to the surface. Analyzing the core generally provides information about the porosity and/or permeability of the rock formation adjacent the wellbore. Cores are generally elongated cylindrical members and obtained with a coring tool having an open barrel for receiving and retaining the core sample.

SUMMARY OF THE INVENTION

Disclosed herein is an example of a method of analyzing a core sample obtained from a wellbore, and which includes scanning the core sample to reveal internal features and structure with a scan source at a location proximate to the wellbore, and estimating information about a formation adjacent the wellbore based on the step of scanning. The step of scanning the core sample can provide such information as relative density of the formation, fracture patterns in the core sample, non-homogeneous regions in the core sample, and combinations thereof; depending on the inner features that can be examined. The method in this example can further include estimating fracture patterns in the formation based on the step of scanning. The method can also include scanning a strategically selected portion of the core sample with a scan source that scans to a nano-scale and that obtains a nanostructural make-up of material making up the core sample. Embodiments exist where an "area of interest" of the core sample is identified based on the step of scanning. Alternatively, the area of interest of the core sample is separated from the core sample, where examples of separating the area of interest of the core sample include obtaining a wafer from the core sample, obtaining a plug from the core sample, crushing material from the core sample, pelletizing the core sample, and combinations thereof. After separating the area of interest, all or a portion of it can be analyzed with a spectrometer. An example of a spectrometer is a laser induced breakdown spectroscope and that is used to identify elements of material making up the core sample. Another example of a spectrometer is a Raman spectrometer and that is used to classify organic compounds of material making up the core sample. Yet another example of a spectrometer is a near infrared spectrometer and that is used to estimate water content of material making up the core sample. Alternatively, a permeability of the formation is estimated based on the step of scanning the core sample. In an embodiment, scanning the core sample with a scan source includes a first scan, the method further including focusing a second scan on a portion of the core sample based on information obtained from the first scan.

Another example method of analyzing a core sample obtained from a wellbore involves obtaining information about a formation adjacent the wellbore by scanning the core sample with a scan system that is at a location proximate the wellbore to reveal internal features and structure, obtaining information about the nano-structure of the core sample by scanning a strategically selected piece of the core sample with a nano-scan system that is at the location proximate the wellbore, and obtaining information about the elemental and mineral makeup of the core sample by analyzing the core sample with a spectrometer that is at the location proximate the wellbore. The scan system can be a computerized tomography scanner. In an embodiment, the spectrometer is a laser induced breakdown spectrometer, a Raman spectrometer, a near infrared spectrometer, or combinations thereof. The spectrometer can be used to identify elements in the core sample, identify water in the core sample, or to classify organic compounds in the core sample. The method may optionally include modeling a hydrocarbon bearing reservoir in the formation.

An example of a system for analyzing a core sample obtained from a wellbore is also disclosed herein and which includes an X-ray scan system that selectively directs radiation into the core sample and monitors radiation scattered from the core sample, and that is disposed at a location adjacent the wellbore, a nano-scan system that selectively directs radiation into the core sample and monitors radiation scattered from the core sample to identify nano-structural information about the core sample, and a spectrometer disposed at the location adjacent the wellbore and that selectively analyzes material making up the core sample. The X-ray scan system, nano-scan system, and spectrometer can be in enclosures that are disposed on a drilling pad.

BRIEF DESCRIPTION OF DRAWINGS

Some of the features and benefits of the present invention having been stated, others will become apparent as the description proceeds when taken in conjunction with the accompanying drawings, in which.

Figure 1:
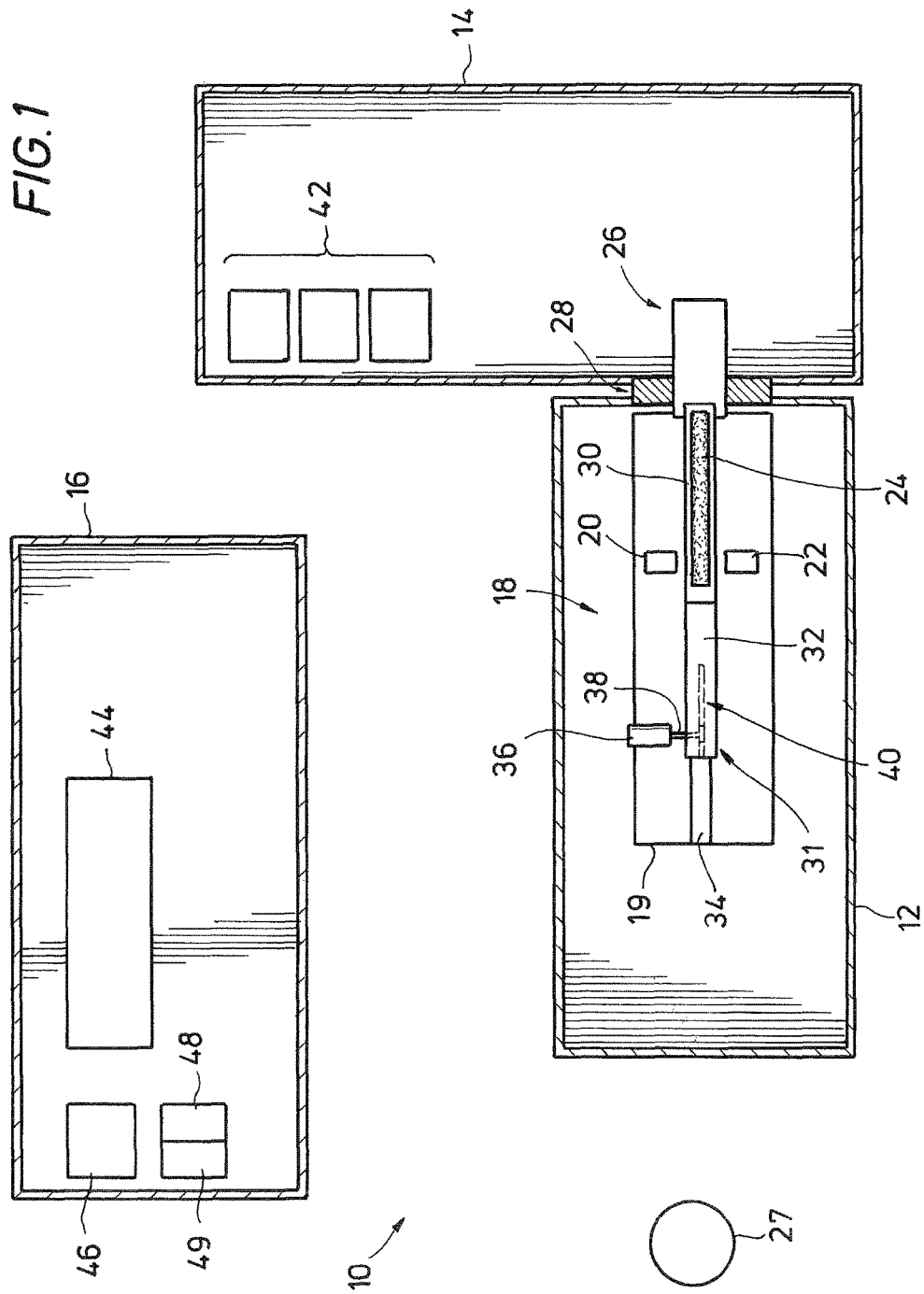
FIG. 1 is a plan partial sectional view of an example of a system for analyzing a core sample.

While the invention will be described in connection with the preferred embodiments, it will be understood that it is not intended to limit the invention to that embodiment. On the contrary, it is intended to cover all alternatives, modifications, and equivalents, as may be included within the spirit and scope of the invention as defined by the appended claims.

DETAILED DESCRIPTION OF INVENTION

The method and system of the present disclosure will now be described more fully hereinafter with reference to the accompanying drawings in which embodiments are shown. The method and system of the present disclosure may be in many different forms and should not be construed as limited to the illustrated embodiments set forth herein; rather, these embodiments are provided so that this disclosure will be thorough and complete, and will fully convey its scope to those skilled in the art. Like numbers refer to like elements throughout. In an embodiment, usage of the term "about" includes, but is not necessarily limited to, +/−5% of the cited magnitude. In an embodiment, usage of the term "substantially" includes but is not necessarily limited to, +/−5% of the cited magnitude.

It is to be further understood that the scope of the present disclosure is not limited to the exact details of construction, operation, exact materials, or embodiments shown and described, as modifications and equivalents will be apparent to one skilled in the art. In the drawings and specification, there have been disclosed illustrative embodiments and, although specific terms are employed, they are used in a generic and descriptive sense only and not for the purpose of limitation.

Shown in a plan partial sectional view in FIG. 1 is one example of a core analysis system 10, which includes first, second and third mobile enclosures. In the example of FIG. 1, the first mobile enclosure is a scan trailer 12, the second mobile enclosure is a handling trailer 14, and the third mobile enclosure is an analysis trailer 16. In one example, each of the enclosures may be part of a uniquely modified trailer and which are movable by a tractor. Schematically illustrated in the scan trailer 12 is a scan system 18, and substantially all of which is housed within a cabinet 19. In the illustrated example, cabinet 19 is specially designed to shield any radiation within, generated, inherent, or otherwise, from making its way to outside of the cabinet 19. Thus, cabinet 19 is in compliance with 21 C.F.R. 1020.40. Further shown in cabinet 19 is a scan source 20, which in one embodiment includes a device for emitting radiation, such as but not limited to an X-ray, microwave, millimeter wave, etc. A scan receiver 22 is also shown provided within cabinet 19 and combined with scan source 20, in one example, forms a Computed Tomography (CT) scanner.

An elongate and cylindrical core sample 24 is shown axially inserted within scan system 18. Core sample 24 is disposed into scan system 18 through a loading assembly 26, which is shown coupled to one end of the scan system 18 and projecting through an opening in a side wall of handling trailer 14. In an example, core sample 24 is taken from a subterranean formation below the core analysis system 10, and is retrieved via a wellbore 27 shown adjacent the core analysis system 10. Thus the wellbore 27 intersects the subterranean formation. Embodiments exist where the core analysis system 10 is "onsite" in the field and where the distance between the wellbore 27 to the core analysis system 10 can range from less than one hundred yards up to five miles, and any distance between. Accordingly, real time analysis while drilling the wellbore 27 can take place within the core analysis system 10. Feedback from the analysis can be used by the drilling operator to make adjustments or changes to the drilling operation.

A hatch assembly 28 is schematically illustrated which provides the coupling interface between trailers 12, 14 and includes sealing around the loading assembly 26. While in scan system 18, core sample 24 rests on a core carrier 30. Core carrier 30 is part of a manipulator system 31, which further includes a manipulator arm 32 that telescopingly moves along a manipulator base 34. As shown, an end of manipulator arm 32 distal from manipulator base 34 couples onto an end of core carrier 30, so that core carrier 30 is basically cantilevered on an end of the manipulator arm 32. Manipulator arm 32 is shown in an extended position over manipulator base 34. Manipulator arm 32 axially moves with respect to manipulator base 34 via a motor 36 shown having a shaft 38 that couples to manipulator arm 32. A gear (not shown) on an end of shaft 38 distal from motor 36 engages a gear rack 40 that is provided on manipulator arm 32. Accordingly, selectively operating motor 36 urges manipulator arm 32, core carrier 30 and core sample 24 in an axial direction with respect to scan source 20. Moving manipulator arm 32 into a retracted position onto manipulator base 34 positions the entire length of core sample 24 in scan system 18, so that all of core sample 24 may be analyzed by the scan system 18. In one example, the scan source 20 and scan receiver 22 orbit around the core sample 24 and so that when in combination of axial movement of core sample 24 within system 18, a computed tomography (CT) helical scan is taken of core sample 24. Further optionally, motor 36, or additional motors not shown, may manipulate and selectively move manipulator arm 32 vertically and/or laterally to thereby better position core sample 24 into a designated orientation and/or spatial position during the scanning process.

Further shown in FIG. 1 are a series of work surfaces 42 provided within handling trailer 14. In one example of operation, before or after core sample 24 is scanned, it may be broken into sections for further analysis and analyzed on work surfaces 42. Examples of the work surfaces 42 include a crusher, sample divider, and mortar grinder. Additional analysis may take place within analysis trailer 16. Schematically illustrated within analysis trailer 16 are a variety of analysis equipment such as, but not limited to, scanners and spectrometers. One such analysis equipment is a NANO-TOM® 44, which can include a scanning system for scanning the internals of core sample 24, or parts of the core sample 24. Further analysis equipment in the analysis trailer 16 may be a laser induced breakdown spectroscope 46, a Raman spectroscope 48, and near infrared spectroscope 49. It will be understood that alternate embodiments may include more trailers or fewer trailers. For example, an appropriately sized scan system 18 may allow loading assembly 26 to be in scan trailer 12 without projecting through an opening in the scan trailer 12 and without a hatch assembly 28. A further embodiment may provide work surfaces 42 in the same trailer as the analysis equipment, or the analysis equipment may be contained in handling trailer 14. In yet a further embodiment, scan system 18, loading assembly 26, work surfaces 42 and analysis equipment (e.g., NANOTOM® 44, spectroscopes 46, 48, 49, or others) are all contained in one trailer.

Figure 2:
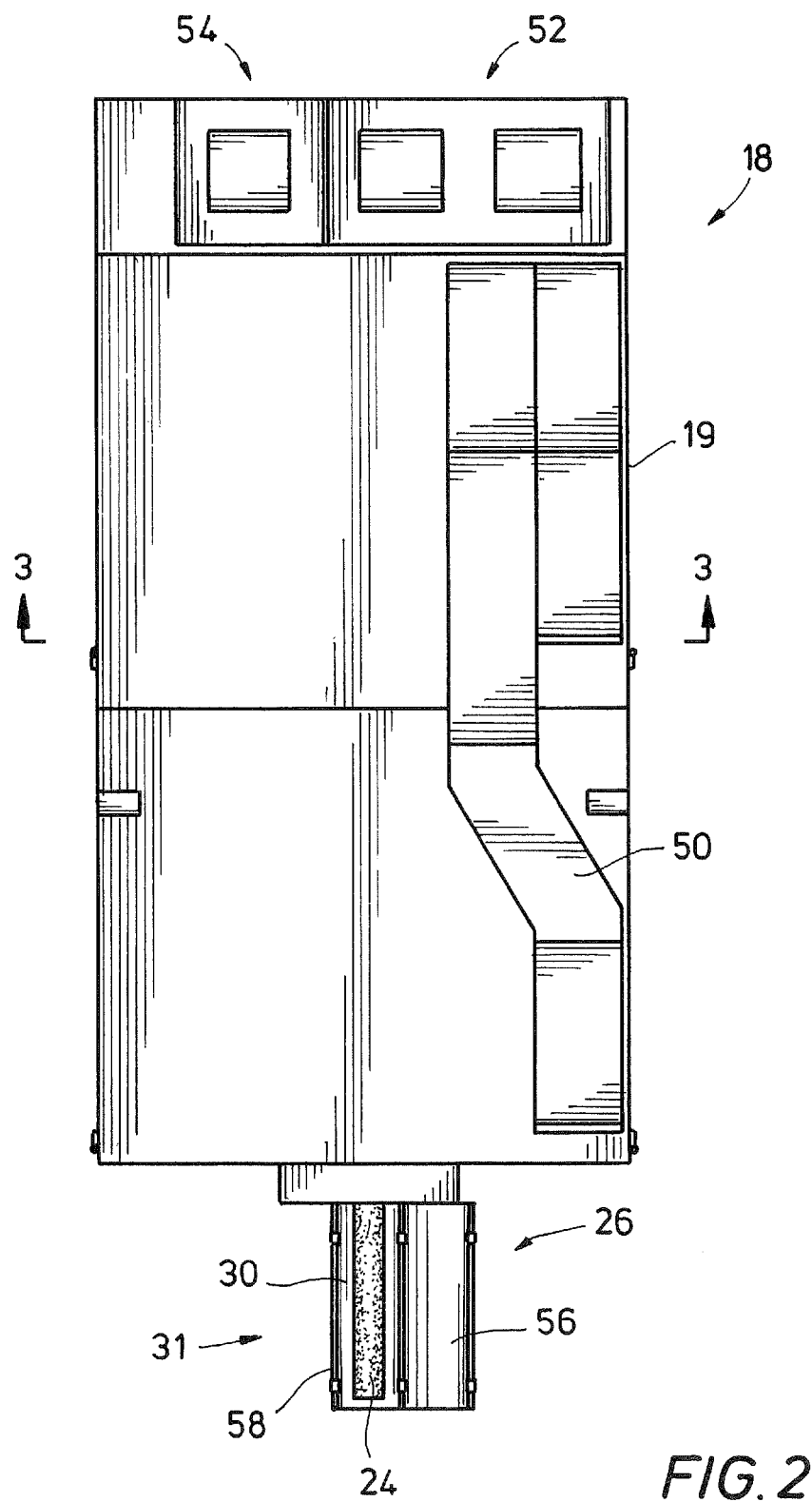
FIG. 2 is an overhead view of an example of a cabinet for shielding radiation from a scanning unit for a core sample.

Referring now to FIG. 2, shown in an overhead view is an example of the scan system 18 and an upper surface of cabinet 19. Further illustrated in this example is a conditioning vent 50 on an upper end of the cabinet 19, where conditioning vent 50 provides a path for airflow and that is used in conditioning the inside of the cabinet 19, while blocking the leakage of radiation from cabinet 19. An advantage of the conditioning vent 50 is that conditioned air at proper temperature and humidity may be injected into the inside of cabinet 19 so that the sensitive devices housed within the cabinet 19 may be maintained in proper operating conditions to ensure normal operating functionality. In an example, operation conditions require maintaining temperature within 2 degrees C., in spite of substantial air replacement due to loading mechanism operation, temperature uniformity is maintained across the scanner frame and rotary element. A power distribution panel 52 is shown provided at an aft end of cabinet 19, and which includes buses (not shown) and other devices for distributing power through cabinet 19 into scan system 18. A control panel 54 is shown adjacent power distribution panel 52 and includes hardware and software for managing control of the operation of the systems house within cabinet 19. Projecting outward past the forward end of cabinet 19 is the loading assembly 26 in an open configuration. In the illustrated example, the loading assembly 26 includes a loading cover 56 and loading basin 58, where the loading cover 56 is shown swung open from a loading basin 58. As shown the core sample 24 has been inserted into open loading assembly 26 and onto the core carrier 30. As will be described in more detail below, safety features are included with the core analysis system 10 that prevent operation of the manipulator system 31 when the loading assembly 26 is in the open position of FIG. 2.

Figure 3:
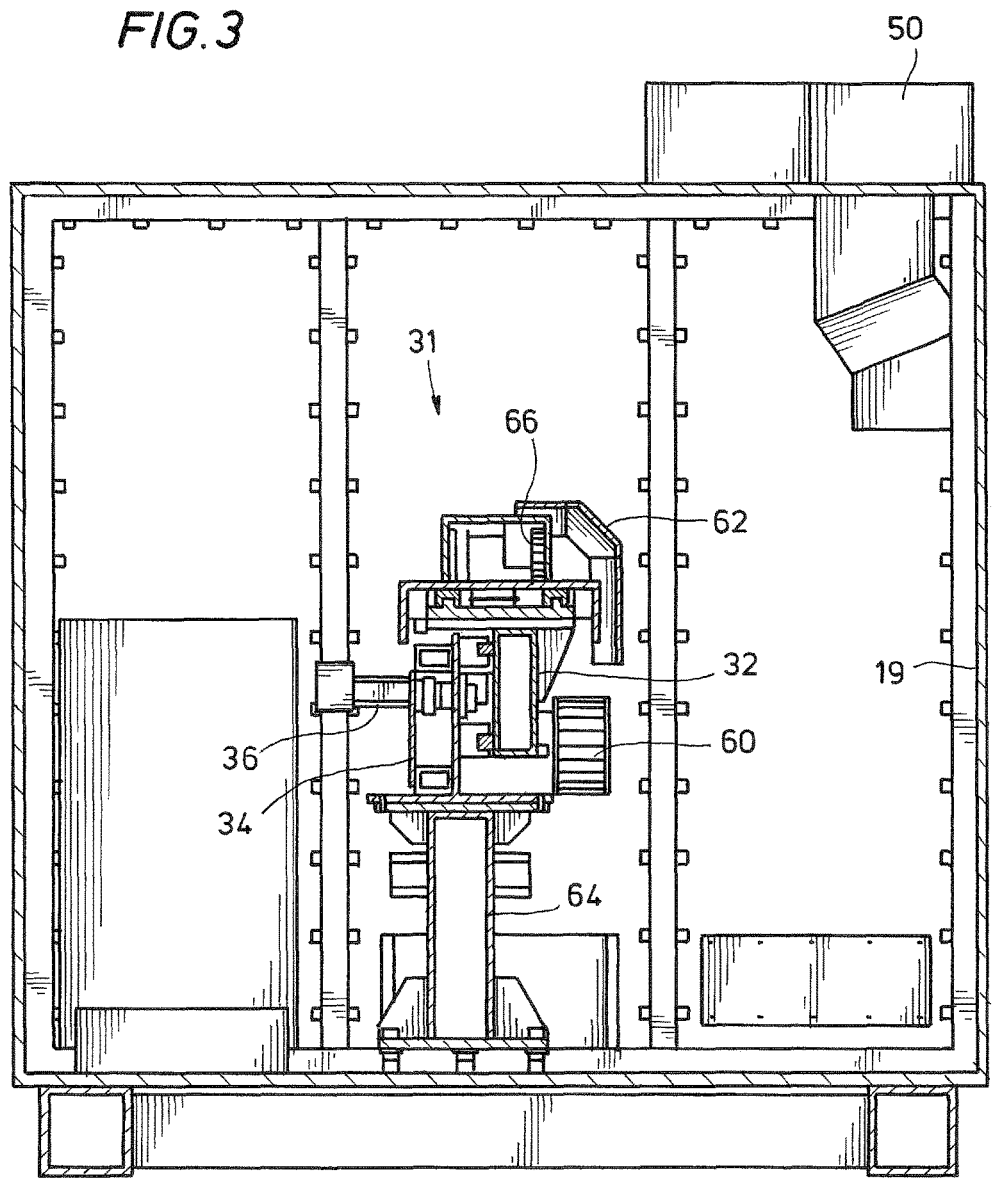
FIG. 3 is an axial sectional view of the cabinet of FIG. 2 and taken along lines 3-3.

FIG. 3 shows an example of the cabinet 19 in a sectional view and taken along lines 3-3 of FIG. 2. This view which is taken along the axial portion of manipulator system 31 shows one example of a wiring track 60; which has cross members for organizing the control and power wires needed for use in the scan system 18 and as the manipulator arm 32 axially moves with respect to manipulator base 34. Wiring track 60 maintains the wires in a designated location and position with use of wiring track 60 during operation of the manipulator system 31. Further in the example of FIG. 3 is a shroud 62 shown mounted on an upper end of manipulator system 31 and which covers a portion of the upper end and shields components within the manipulator system 31. Manipulator base 34 (and thus manipulator arm 32) is supported on a vertical mounting pedestal 64, which has a generally rectangular cross section along its axis, and has a lower end mounted on the floor of cabinet 19. Shown housed within shroud 62 is a wiring bus 66 which extends axially along the manipulator base 34.

Figure 4:
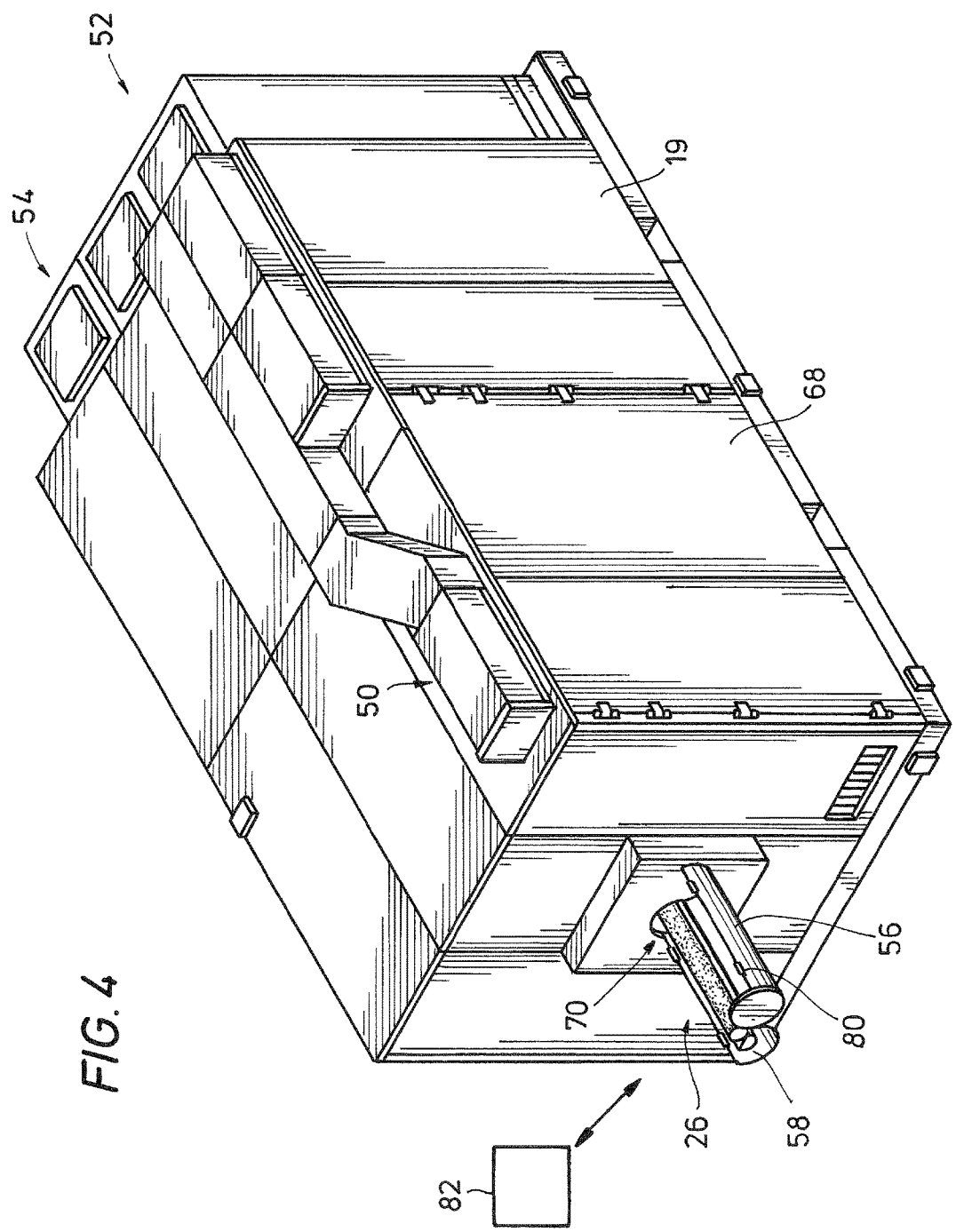
FIG. 4 is a perspective view of the cabinet of FIG. 2.

FIG. 4 provides in perspective view of one example of the cabinet 19 and having hinged panel 68 along its outer surface. As indicated above, the structure of cabinet 19 is in compliance with 21 C.F.R. 1020.40. Thus proper protective shielding and interlocking is provided in the panel 68 and along the hinged interface. An additional safety feature is a door assembly 70 which includes a barrier (not shown) that slides axially across the opening shown at the base of the loading assembly 26 and in a forward wall of cabinet 19. The barrier thus provides a radiation shield from the inside to the outside of cabinet 19 while still allowing core sample 24 loading in compliance with 21 C.F.R. §1020.40.

Figure 5:
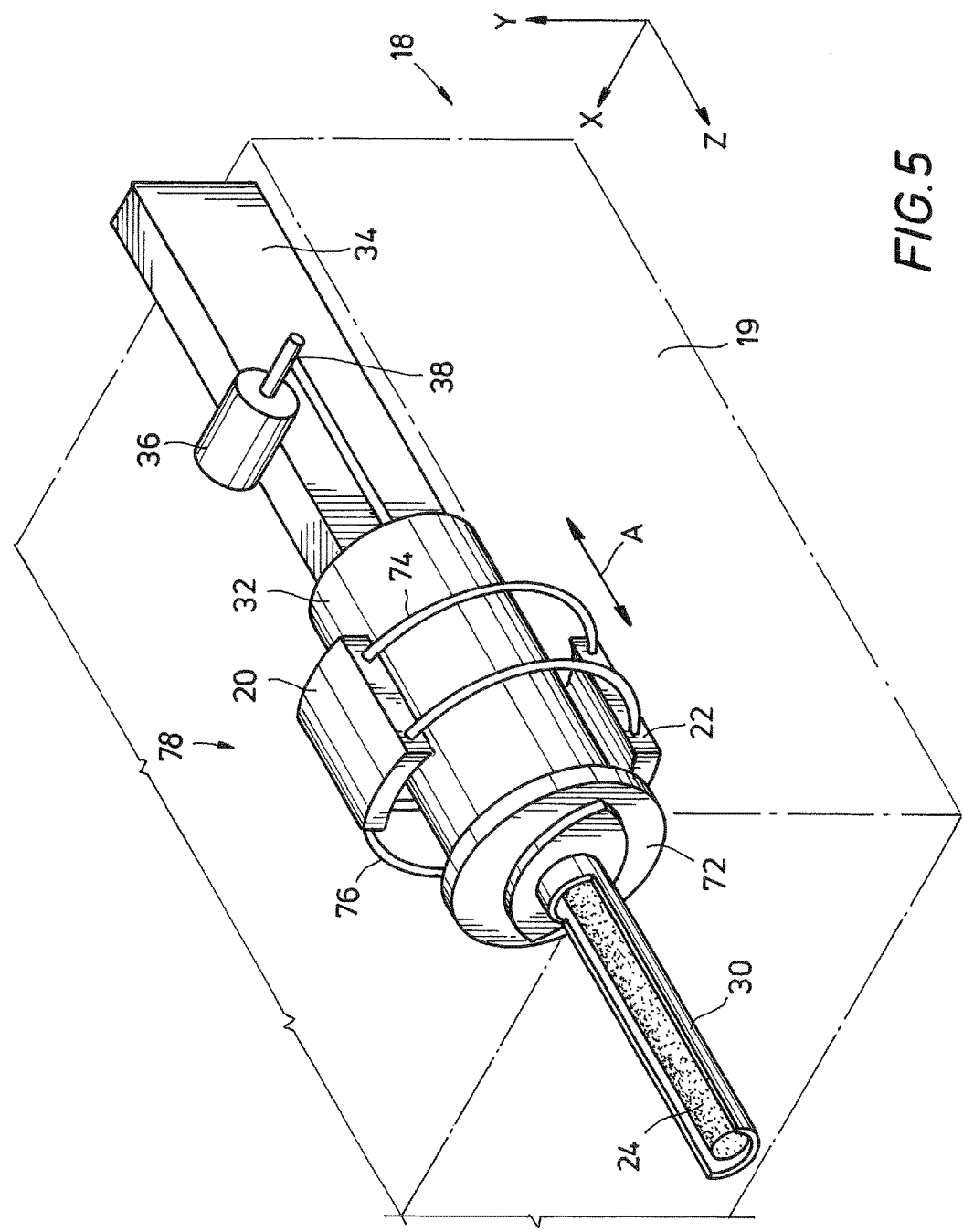
FIG. 5 is a perspective view of the cabinet of FIG. 2 in partial phantom view and an example scanning unit in the cabinet.

An example of the manipulator system 31 within cabinet 19 is illustrated in perspective view in FIG. 5, and where cabinet 19 is shown in a partial phantom view. In this embodiment, a rearward end of manipulator base 34 is supported on a rearward end of cabinet 19; manipulator base 34 extends axially away from the rearward wall of cabinet 19 with the manipulator arm 32 axially sliding on manipulator base 34. Motor 36 is shown oriented generally perpendicular to an axis of manipulator arm 32 and manipulator base 34, and couples to manipulator arm 32 by shaft 38. Further illustrated is how the core carrier 30 couples to a mounting plate 72; where mounting plate 72 is a generally circular and planar member that mounts on a forward end of manipulator arm 32.

Axial movement, as shown by the double headed arrow A, of core sample 24 is accomplished via motor 36. X, Y, and Z axes are illustrated to define an example coordinate system for the purposes of reference herein. While not limited to this coordinate system, the axes depict axial movement of any object, such as the core sample 24, to be along the Z axis, vertical movement to be along the Y axis, and lateral movement to be along the X axis. As indicated above, operation of motor 36 can move core sample 24 along all of these axes. Further shown in FIG. 5 are curved supports 74, 76 that circumscribe manipulator arm 32 and provide a mounting surface for scan source 20 and scan receiver 22. The combination of the curved supports 74, 76 define a gantry 78 that when rotated puts the scan source 20 and scan receiver 22 at an orbiting rotation around the core sample 24 and provides the scanning capabilities of the scan system 18.

Referring back to FIG. 4, an interlock connector 80 is shown provided on the loading cover 56 and loading basin 58. The interlock connectors 80 thus may recognize when the cover 56 is in the open position of FIG. 4 and in combination with controller 82 may prevent operation of the manipulator system 31. However, the control system (for example, controller 82) associated with the scan system 18 that allows for motion of the manipulator system 31 when the loading cover 56 is in the closed position and interlock connectors 80 are adjacent one another.

Figure 6:
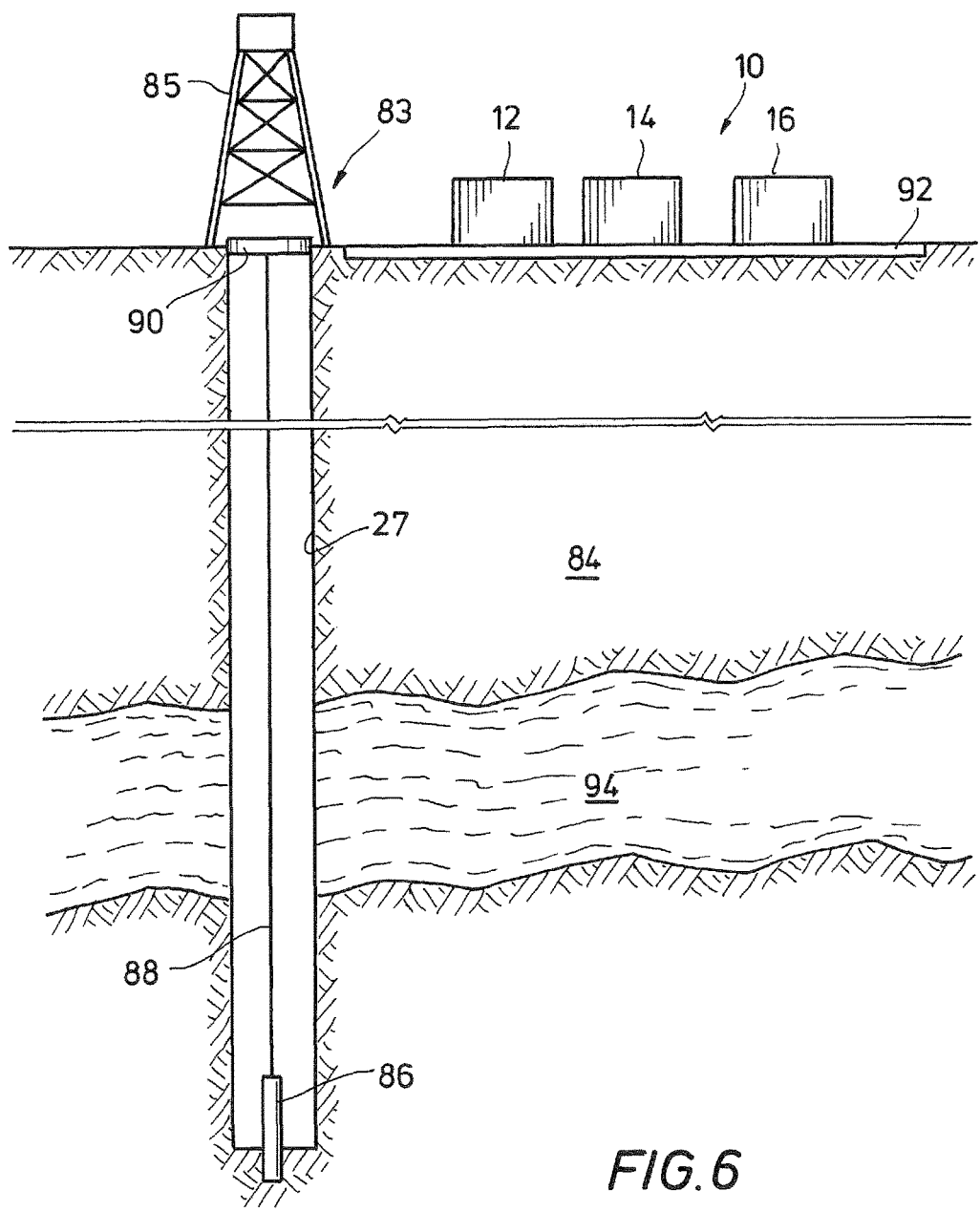
FIG. 6 is a partial sectional view of an example of a drilling system obtaining a core sample from a wellbore.

Shown in partial side sectional view in FIG. 6 is an example of a drilling system 83 for obtaining a core sample 24 (FIG. 1) from within the wellbore 27. As shown, wellbore 27 intersects a formation 84, which in an example may extend underneath core analysis system 10. In the example, the drilling system 83 includes a derrick 85 mounted on surface and above the opening of the wellbore 27. A coring bit 86 is shown on a lower end of a drill string 88 which is used to obtain sample cores from within formation 84. A rotary table 90 is shown with the derrick 85 and in this embodiment is used for rotating the drill string 88 and coring bit 86.

Further in the example of FIG. 6, a drilling pad 92 is provided on surface and adjacent the wellbore 27. The drilling pad 92 as shown provides a location on which the core analysis system 10 is disposed. Thus the scan trailer 12, handling trailer 14, and analysis trailer 16 are on the drilling pad 92 and proximate the wellbore 27 to enable the real time analysis of the core sample 24 (FIG. 1) as travel to a location remote from the wellbore 27 is unnecessary for analyzing the core sample 24.

Referring back to FIG. 1, in one example of operation, the core sample 24 is scanned in scan system 18. Example data obtained from the scanning step includes relative density of the core sample 24, potential fracture patterns in the formation 84 (FIG. 6), and non-homogenous regions in the core sample 24. In one optional embodiment, after scanning the core sample 24, areas for further investigation in the core sample 24 are identified from analyzing the scan results. Thus a second scan in the scan system 18 can be performed, where the scan is focused on the areas for further investigation in the core sample 24. In this embodiment, selective adjustments to the motor 36 can be done in order to position the core sample 24 at a designated position and/or orientation in the scan system 18. For example, the elevation, lateral position, as well as axial location may be adjusted. Further optionally, the speed at which the scan is performed can be adjusted or varied to obtain enhanced resolution of scan data in particular locations in the core sample 24. Similarly, the scan of the core sample 24 can be adjusted to avoid areas with inclusions or contamination that cause distortion in the results.

In one embodiment, the sequence of analysis may be to first scan the core sample 24 with the scan system 18, then in the following order, scan the core sample 24 with the NANOTOM® 44, scan with the laser-induced breakdown spectroscopy 46, scan with the Raman spectroscope 48, and scan with the near infrared spectroscope 49. Optionally, based on the first scan an "area of interest" can be identified for further study. In one example, the area of interest of the core sample 24 is removed and scanned with the NANOTOM® 44 and analyzed with the spectrometers. In one non-limiting example of operation, removing the area of interest can include cutting wafers that are 5 mm×1.5", forming plugs that are less than 4 cm in length, crushing the plugs to a particulate size of less than 0.1 cm, grinding to a particulate size of less than 50 microns, drying the 50 micron samples, and generating pellets having a width of 31 mm. An advantage of scanning and analyzing the core sample 24 with the above devices is the ability to obtain information about the formation while the step of drilling the wellbore 27 is in process. Thus adjustments in the drilling process can be made. Further, the real time information can be used for modeling a hydrocarbon bearing reservoir 94 (FIG. 6), site planning, or strategy for completing the wellbore 27, such as where to perforate the wellbore 27 and/or where to not perforate the wellbore 27.

Information that can be gleaned by using the NANOTOM® 44 includes the microscopic structure of the material, and the nano-structure of down to 300 nm in length. The laser-induced breakdown spectroscopy 46 can yield information about the elements in the core sample 24, whereas the Raman spectroscope 48 can help to classify the organic compounds present in the core sample 24. The near infrared spectroscope 49 can provide water content of the core sample 24.

The present invention described herein, therefore, is well adapted to carry out the objects and attain the ends and advantages mentioned, as well as others inherent therein. While a presently preferred embodiment of the invention has been given for purposes of disclosure, numerous changes exist in the details of procedures for accomplishing the desired results. It should be pointed out that scanning the core sample 24 includes using one or more of the scan system 18, laser-induced breakdown spectroscopy 46, the Raman spectroscope 48, the near infrared spectroscope 49, and any other manner of obtaining information about the core sample 24. These and other similar modifications will readily suggest themselves to those skilled in the art, and are intended to be encompassed within the spirit of the present invention disclosed herein and the scope of the appended claims.

What is claimed is:

1. A method of analyzing a core sample obtained from a wellbore comprising:
scanning an inside of the core sample with a scan source, the core sample and the scan source both positioned within a mobile enclosure at a location proximate to the wellbore;
estimating information about a formation adjacent the wellbore based on the step of scanning; and
scanning an inside of the core sample with a second scan source that scan to a nano-scale and that obtains a nano-structural make-up of material making up the core sample.

2. The method of claim 1, wherein the step of scanning the inside of the core sample provides information selected from the group consisting of relative density of a formation, fracture patterns in the core sample, non-homogeneous regions in the core sample, and combinations thereof.

3. The method of claim 2, further comprising estimating fracture patterns in the formation based on the step of scanning.

4. The method of claim 1, further comprising fragmenting the core sample.

5. The method of claim 4, wherein the step of fragmenting is selected from the group consisting of obtaining a wafer from the core sample, obtaining a plug from the core sample, crushing material from the core sample, pelletizing the core sample, and combinations thereof.

6. The method of claim 4, further comprising obtaining a fragment from the step of fragmenting the core sample, and analyzing the fragment with a spectrometer.

7. The method of claim 6, wherein the spectrometer is a laser induced breakdown spectroscope and that is used to identify elements of material making up the core sample.

8. The method of claim 6, wherein the spectrometer is a Raman spectrometer and that is used to classify organic compounds of material making up the core sample.

9. The method of claim 6, wherein the spectrometer is a near infrared spectrometer and that is used to estimate water content of material making up the core sample.

10. The method of claim 1, further comprising estimating a permeability of the formation based on the step of scanning the core sample.

11. The method of claim 1, wherein the step of scanning an inside of the core sample with a scan source comprises performing a first scan of the core sample, the method further comprising performing a second scan on a portion of the core sample based on information obtained from the first scan.

12. A method of analyzing a core sample obtained from a wellbore comprising:
obtaining information about a formation adjacent the wellbore by scanning an inside of the core sample with a scan system that is at a location proximate the wellbore;
obtaining information about the nano-structure of the core sample by scanning the inside of the core sample with a nano-scan system that is at the location proximate the wellbore; and
obtaining information about matter inside of the core sample by analyzing the core sample with a spectrometer that is at the location proximate the wellbore.

13. The method of claim 12, wherein the scan system comprises a computed tomography scanner.

14. The method of claim 12, wherein the spectrometer is selected from the list consisting of a laser induced breakdown spectrometer, a Raman spectrometer, a near infrared spectrometer, and combinations thereof.

15. The method of claim 12, further comprising using the spectrometer to identify elements in the core sample, identify water in the core sample, and to classify organic compounds in the core sample.

16. The method of claim 12, further comprising modeling a hydrocarbon bearing reservoir in the formation.

17. A system for analyzing a core sample obtained from a wellbore comprising:
- an X-ray scan system that selectively directs radiation into the core sample and monitors radiation scattered from the core sample, and that is disposed at a location adjacent the wellbore;
- a nano-scan system that selectively directs radiation into the core sample and monitors radiation scattered from the core sample to identify nano-structural information about the core sample; and
- a spectrometer disposed at the location adjacent the wellbore and that selectively analyzes material making up the core sample.

18. The system of claim 17, wherein the system further comprises a drilling pad and the X-ray scan system, nano-scan system, and spectrometer are in enclosures that are disposed on the drilling pad.

\* \* \* \* \*